(12) United States Patent
Blaeser et al.

(10) Patent No.: US 9,155,608 B2
(45) Date of Patent: Oct. 13, 2015

(54) DEVICES AND METHODS FOR TREATMENT OF OBESITY

(76) Inventors: David Blaeser, Brooklyn Park, MN (US); Dale Spencer, Wayzata, MN (US)

(*) Notice: Subject to any disclaimer, the term of this patent is extended or adjusted under 35 U.S.C. 154(b) by 532 days.

(21) Appl. No.: 12/677,227

(22) PCT Filed: Sep. 12, 2008

(86) PCT No.: PCT/US2008/076126
§ 371 (c)(1),
(2), (4) Date: Apr. 28, 2010

(87) PCT Pub. No.: WO2009/036244
PCT Pub. Date: Mar. 19, 2009

(65) Prior Publication Data
US 2011/0009801 A1    Jan. 13, 2011

Related U.S. Application Data

(60) Provisional application No. 60/971,729, filed on Sep. 12, 2007.

(51) Int. Cl.
*A61F 2/04* (2013.01)
*A61B 19/00* (2006.01)
(Continued)

(52) U.S. Cl.
CPC ............... *A61F 2/04* (2013.01); *A61B 17/064* (2013.01); *A61B 17/0644* (2013.01); *A61F 5/0076* (2013.01); *A61B 2017/00818* (2013.01); *A61F 2002/045* (2013.01)

(58) Field of Classification Search
CPC ....................................................... A61F 2/04
USPC ..................................................... 604/8, 317
See application file for complete search history.

(56) References Cited

U.S. PATENT DOCUMENTS

| 4,134,405 A | 1/1979 | Smit |
|---|---|---|
| 4,315,509 A | 2/1982 | Smit |

(Continued)

FOREIGN PATENT DOCUMENTS

| WO | WO 2006/044640 A1 | 4/2006 |
|---|---|---|
| WO | WO 2007/017872 A2 | 2/2007 |
| WO | WO 2008/030403 A1 | 3/2008 |

OTHER PUBLICATIONS

"Average Knot-Pull Limits of Various Sizes and Diameters of Sutures". US Pharmacopeia NF24 pp. 2052. <http://www.pharmacopeia.cn/v29240/usp29nf24s0_m80200.html>. See attached document.*

(Continued)

*Primary Examiner* — Tatyana Zalukaeva
*Assistant Examiner* — Sara Sass
(74) *Attorney, Agent, or Firm* — Popovich, Wiles & O'Connell, P.A.

(57) ABSTRACT

A device for isolating tissue in the digestive tract including a biocompatible portion having a surface sized to cover the tissue to be isolated and also includes a plurality of micro-anchors attached to the biocompatible portion and extending from the surface, the micro-anchors sized to penetrate the mucosa of the tissue. A method for isolating tissue in the digestive tract in which an isolation element is delivered to a desired location in the digestive system; the isolation element having fixed thereto a plurality of micro-anchors. The method also includes attaching the isolation element to tissue at the desired location by causing the micro-anchors to penetrate the mucosa of the tissue.

51 Claims, 8 Drawing Sheets

(51) Int. Cl.
*A61F 2/36* (2006.01)
*A61B 17/064* (2006.01)
*A61F 5/00* (2006.01)
*A61B 17/00* (2006.01)

(56) References Cited

U.S. PATENT DOCUMENTS

| | | | |
|---|---|---|---|
| 4,501,264 A | 2/1985 | Rockey | |
| 4,641,653 A | 2/1987 | Rockey | |
| 4,763,653 A | 8/1988 | Rockey | |
| 5,306,300 A | 4/1994 | Berry | |
| 5,820,584 A | 10/1998 | Crabb | |
| 5,950,633 A | 9/1999 | Lynch et al. | |
| 6,254,642 B1 * | 7/2001 | Taylor | 623/23.64 |
| 6,355,056 B1 | 3/2002 | Pinheiro | |
| 6,675,809 B2 | 1/2004 | Stack et al. | |
| 6,740,121 B2 | 5/2004 | Geitz | |
| 6,946,002 B2 | 9/2005 | Geitz | |
| 7,025,791 B2 | 4/2006 | Levine et al. | |
| 7,111,627 B2 | 9/2006 | Stack et al. | |
| 7,121,283 B2 | 10/2006 | Stack et al. | |
| 7,122,058 B2 | 10/2006 | Levine et al. | |
| 7,152,607 B2 | 12/2006 | Stack et al. | |
| 7,175,669 B2 | 2/2007 | Geitz | |
| 7,211,114 B2 | 5/2007 | Bessler et | |
| 7,220,284 B2 | 5/2007 | Kagan et al. | |
| 7,846,138 B2 * | 12/2010 | Dann et al. | 604/263 |
| 2003/0040804 A1 | 2/2003 | Stack et al. | |
| 2003/0040808 A1 | 2/2003 | Stack et al. | |
| 2003/0093117 A1 | 5/2003 | Saadat | |
| 2003/0199989 A1 | 10/2003 | Stack et al. | |
| 2004/0092892 A1 | 5/2004 | Kagan et al. | |
| 2004/0093065 A1 | 5/2004 | Yachia et al. | |
| 2004/0107004 A1 | 6/2004 | Levine et al. | |
| 2004/0172142 A1 | 9/2004 | Stack et al. | |
| 2004/0220682 A1 | 11/2004 | Levine et al. | |
| 2004/0237736 A1 | 12/2004 | Genova et al. | |
| 2005/0004681 A1 | 1/2005 | Stack et al. | |
| 2005/0049718 A1 | 3/2005 | Dann et al. | |
| 2005/0075622 A1 | 4/2005 | Levine et al. | |
| 2005/0080395 A1 | 4/2005 | Levine et al. | |
| 2005/0085787 A1 | 4/2005 | Laufer | |
| 2005/0085923 A1 | 4/2005 | Levine et al. | |
| 2005/0125020 A1 | 6/2005 | Meade et al. | |
| 2005/0125075 A1 | 6/2005 | Meade et al. | |
| 2005/0221072 A1 * | 10/2005 | Dubrow et al. | 428/292.1 |
| 2006/0009858 A1 | 1/2006 | Levine et al. | |
| 2006/0064120 A1 | 3/2006 | Levine et al. | |
| 2006/0161172 A1 | 7/2006 | Levine et al. | |
| 2006/0161187 A1 | 7/2006 | Levine et al. | |
| 2006/0206063 A1 | 9/2006 | Kagan et al. | |
| 2006/0206064 A1 * | 9/2006 | Kagan et al. | 604/264 |
| 2006/0265082 A1 | 11/2006 | Meade et al. | |
| 2007/0005147 A1 | 1/2007 | Levine et al. | |
| 2007/0032879 A1 | 2/2007 | Levine et al. | |

OTHER PUBLICATIONS

In Sep. 25, 2012 Office Action, "Average Knot-Pull Limits of Various Sizes and Diameters of Sutures". US Pharmocopeia NF24 pp. 2052. <http://www.pharmacopeia.cn/v29240/usp29nf24s0_m80200.html>. Nov. 27, 2010.*

Jan. 26, 2009 International Search Report and Written Opinion for PCT Application No. PCT/US08/076126 (11 pages).

Dec. 2, 2011 European Search Report for corresponding Application No. 08830976.0 (5 pages).

* cited by examiner

DEVICES AND METHODS FOR TREATMENT OF OBESITY

This application claims the benefit of U.S. Provisional Application No. 60/971,729, filed Sep. 12, 2007, entitled "Devices and Methods for Treatment of Obesity", the contents of which are hereby incorporated by reference.

BACKGROUND OF THE INVENTION

The present invention relates to devices and methods for attachment of a device within a patient's digestive tract. In particular, the present invention relates to devices and methods for treatment of obesity and/or its comorbidities, such as diabetes.

According to the Center for Disease Control (CDC), sixty six percent of the United States population is overweight, and thirty two percent are obese, presenting an overwhelming health problem. From an economic standpoint, it is estimated that more than 100 billion dollars are spent on obesity and treating its major co-morbidities. This does not even consider the psychological and social costs of this epidemic problem. In the opinion of many health care experts, obesity is the largest health problem facing westernized societies and is considered an epidemic. From a medical standpoint, obesity is the primary risk factor for type 2 diabetes and obstructive sleep apnea. It increases the chances for heart disease, pulmonary disease, infertility, osteoarthritis, cholecystitis and several major cancers, including breast and colon. Despite these alarming facts, treatment options for obesity remain limited.

Treatment options include dietary modification, very low calorie liquid diet, pharmaceutical agents, counseling, exercise programs and surgery. Diet and exercise plans fail since most individuals do not have the discipline to adhere to such plans. When diet and exercise fail many try dietary supplements and drugs or other ingestible preparations promoted as being capable of suppressing appetite or inducing satiety. In general, these techniques for treating compulsive overeating/obesity have tended to produce only a temporary effect. The individual usually becomes discouraged and/or depressed after the initial rate of weight loss plateaus and further weight loss becomes harder to achieve. The individual then typically reverts to the previous behavior of compulsive overeating.

Surgical procedures that restrict the size of the stomach and/or bypass parts of the intestine are the only remedies that provide lasting weight loss for the majority of morbidly obese individuals. Surgical procedures for morbid obesity are becoming more common based on long-term successful weight loss result.

Bariatric surgery is a treatment for morbid obesity that involves alteration of a patient's digestive tract to encourage weight loss and to help maintain normal weight. Known bariatric surgery procedures include jejuno-ileal bypass, jejuno-colic shunt, biliopancreatic diversion, gastric bypass, Roux-en-Y gastric bypass, gastroplasty, gastric banding, vertical banded gastroplasty, and silastic ring gastroplasty. A more complete history of bariatric surgery can be found in U.S. Patent Application Publication No. 2004/0092892 A1 Apparatus and Methods for Treatment of Morbid Obesity and also on the website of the American Society for Bariatric Surgery at http://www.asbs.org.

The surgeries which create malabsorption, such as the bypass operation, although effective in weight reduction, involve permanent modification of the GI tract and have a risk of short and long term complication and even death.

The most common weight loss operation in the United States is the Gastric Bypass. These procedures reduce the size of the stomach plus shorten the effective-length of intestine available for nutrient absorption. With gastric bypass many investigators have reported weight loss results that exceed 70% of excess weight. However, this efficacy does not come without complication. The accepted mortality of the procedure is 1 in 200.

Medical sleeve devices for placement in a patient's stomach are described by Rockey in U.S. Pat. Nos. 4,501,264, 4,641,653 and 4,763,653. The medical sleeve described in these patents are said to reduce the surface area available for absorption in the stomach. Other sleeve devices for placement in a patient's intestines are described in U.S. Pat. No. 4,134,405 (Smit), U.S. Pat. No. 4,315,509 (Smit), U.S. Pat. No. 5,306,300 (Berry), and U.S. Pat. No. 5,820,584 (Crabb). The sleeve devices described in these patents are said to be placed at the lower end of the stomach.

Other less invasive techniques for restricting absorption have been suggested. They include bariatric sleeve devices such as those disclosed in US Patent Application Publication Nos. 2004/0092892 to Kagan, et al. and 2004/0107004 to Levine, et al. In these techniques, sleeves are passed through the duodenum so that chyme are passed through the sleeve and do not interact with the absorptive walls of the intestine. The sleeve of the '004 application includes a stent in the pylorus. Another example is Meade et al., U.S. patent application Ser. No. 10/339,786. Other devices to reduce absorption in the small intestines have been proposed (See U.S. Pat. No. 5,820,584 (Crabb), U.S. Pat. No. 5,306,300 (Berry) and U.S. Pat. No. 4,315,509 (Smit)).

In U.S. Patent Application US 2003/0040804, Stack et al. describe a satiation device to aid in weight loss by controlling feelings of hunger. The patent application describes an antral tube that expands into the antrum of the stomach to create a feeling of satiation. In U.S. Patent Application US 2003/0040808, Stack et al. describe a satiation device for inducing weight loss in a patient that includes a tubular prosthesis positionable such that an opening at its proximal end receives masticated food from the esophagus, and such that the masticated food passes through the pouch and into the stomach via an opening in its distal end.

SUMMARY OF THE INVENTION

Insertion of foreign bodies into the digestive tract is difficult. There are strong muscular contractions called peristalsis that drive food down the digestive tract. These forces will make devices difficult to anchor. Thus they will migrate and kink and cause intestinal obstruction. The current invention overcomes this problem by providing an implant that is very compliant or flexible and by distributing the force that the implant is subjected to at the attachment point over a relatively large area.

There is provided in accordance with one aspect of the present invention, an isolation element which is attached to the mucosal side of a wall of the digestive tract.

There is provided in accordance with one aspect of the present invention, a method of attaching a device to the mucosal side of a wall of the digestive tract wherein the attachment means employs nano-technology to achieve adherence of the implant to the wall of the digestive tract. This is achieved by incorporating into the implant nanofibers, such as those developed by NanoSys Inc. to create a so called "gecko" effect. This technology is described in detail in U.S.

Patent Application Publication No. US 2005/0221072, the contents of which are incorporated by reference herein in their entirety.

There is provided in accordance with one aspect of the present invention, a method of attaching an isolation element to the mucosal side of a wall of the digestive tract using an attachment means which employs micro-technology to achieve adherence of the implant to the wall of the digestive tract. A plurality of miniature elements which function as "micro-anchors" are incorporated into the isolation element. These micro-anchors penetrate and engage the tissues that make up the wall of the digestive tract.

There is provided in accordance with one aspect of the present invention, an isolation element which is generally configured of a thin walled cylindrical tube. This isolation element can be made of a multitude of appropriately chosen materials such as silicone or polyurethane. The isolation element is flexible or compliant so that it will not restrict the natural movements of the elements of the digestive tract.

There is provided in accordance with one aspect of the present invention, an isolation element which is generally configured of a thin walled strip of material. This configuration will achieve the affect of allowing contact of ingested food to some portions, circumferentially, of the digestive tract and not allow it in other locations. This configuration and others discussed herein are made possible by sealing all or part of the isolation element to the wall of the digestive tract. This allows isolation of discrete portions of the wall of the digestive tract.

There is provided in accordance with one aspect of the present invention, an isolation element which is generally configured of a series of thin walled cylindrical tubes. At least two of these isolation elements are placed in the digestive tract and spaced a finite distance from one another i.e. there is a finite space between the distal end of one isolation element and the proximal end of the next isolation element. It should be appreciated that this configuration can be repeated as many times as needed. This configuration will achieve the affect of allowing contact of ingested food to some portions of the digestive tract and not allow it in other locations.

There is provided in accordance with one aspect of the present invention, an isolation element which is generally configured of a thin walled cylindrical tube. This isolation element can be configured with portions of the tube having cutouts or windows. These cutouts will achieve the affect of allowing contact of ingested food to some portions of the digestive tract and not allow it in other locations. This type of configuration is made possible by effectively sealing the isolation tube to the wall of the digestive tract around the openings in the isolation element, thus allowing exposure of the wall only at the location of the openings.

There is provided in accordance with one aspect of the present invention, an isolation element which is generally configured of thin walled patch. This patch would not extend circumferentially. It should be appreciated that the patch could be configured to be irregularly shaped. It should be appreciated that this configuration can be repeated as many times as needed throughout the digestive tract. This configuration will achieve the affect of allowing contact of ingested food to some portions of the digestive tract and not allow it in other locations.

There is provided in accordance with one aspect of the present invention, an isolation element which is attached to the digestive tract wall at a discrete location about the proximal end of the isolation element.

There is provided in accordance with one aspect of the present invention, an isolation element which is attached to the digestive tract wall along the entire length of the isolation element.

There is provided in accordance with one aspect of the present invention, an isolation element which is attached to the digestive tract wall along the entire length of the isolation element, but not encircling the isolation element, thus leaving longitudinal potions of the isolation element unattached to the tissue.

There is provided in accordance with one aspect of the present invention, an isolation element which is attached to the digestive tract wall at discrete locations along the length of the isolation element.

There is provided in accordance with one aspect of the present invention, an isolation element which is made of a material that is bioabsorbable or biodegradable. Such a device would have the affect of dissolving over time leaving the patient with a relatively natural digestive system.

There is provided in accordance with one aspect of the present invention, an isolation element which has incorporated into the internal surface elements that create the effect of making the surface lubricous. Nanotechnologies such as those created by NanoSys Inc. or hydrophilic coatings such as a hydrogel could be employed to ensure unobstructed flow of ingested foods.

There is provided in accordance with one aspect of the present invention, an isolation element which is made up entirely of nanostructures such as nano-spheres or particles. These nano-spheres are attached to the wall of the digestive system selectively. The nano-spheres would create a barrier that would limit contact of ingested food with the tissue in the location of the attached nanotechnology. The nano-spheres are incorporated into a dissolvable material and are delivered by placing the material in contact with the tissue in the digestive system that is to be isolated from food contact. The dissolvable material dissolves leaving behind the nano-spheres which remains attached to the tissue.

The invention further includes the methods by which the various isolation elements are delivered and attached to the tissue of the digestive system which is to be isolated.

In one aspect the present invention is a method of isolating tissue in the digestive tract. The method includes delivering an isolation element to a desired location in the digestive system, the isolation element having fixed thereto a plurality of micro-anchors. The method also includes attaching the isolation element to tissue at the desired location by causing the micro-anchors to penetrate the mucosa of the tissue.

The method of isolating tissue in the digestive tract may include the isolation element having a plurality of spaced apart cylindrical tubes. The plurality of cylindrical tubes may have a length in the range of about 2 to 8 cm and/or may be spaced apart by a distance in the range of about 1 to 4 cm. The plurality of cylindrical tubes may further include a proximal tube having proximal and distal ends and a distal tube having proximal and distal ends. The isolation element may be delivered such that the distal end of the proximal tube is located in the pyloric canal, or the isolation element may be delivered such that the proximal end of the distal tube is located adjacent and distal to the pyloric valve, or further the isolation element may be delivered such that the proximal end of the distal tube is located just distal of the orifice of the common bile duct.

The isolation element of the method of isolating tissue in the digestive tract may include at least one longitudinal strip of material or may include at least one patch of material. The at least one patch of material may have an irregular shape or may be sized to cover an area of tissue about 1 to 5 square centimeters.

The method of isolating tissue in the digestive tract may include that the isolation element is a cylindrical tube that may further be provided with cutouts or open portions.

The method may include the micro-anchors being positioned about a proximal end of the isolation element or may include the micro-anchors being positioned at discrete locations along the length of the isolation element. The method may include the microanchors having a length in the range of about 0.013 to 0.254 cm (0.005 to 0.100 inches). The method may include that the micro-anchors have a transverse cross-sectional dimension in the range of about 0.003 to 0.038 cm (0.001 to 0.015 inches). The plurality of micro-anchors of the method may include about 500 to 3000 micro-anchors per square inch and/or the micro-anchors of the method may be made of stainless steel, Nitinol, or a polymer material. The micro-anchors may include protruding scales, the scales having tips that are oriented in a direction substantially opposite to the direction of tips of the micro-anchors. The micro-anchors may be U-shaped having first and second ends oriented in the same direction.

The isolation element of the method of isolating tissue in the digestive tract may be made of silicone or polyurethane and/or may be bioabsorbable or biodegradable. The isolation element of the method may include an internal surface and wherein the internal surface is lubricious or may include a proximal end and a distal end and wherein the isolation element is delivered such that the proximal end is located in the esophagus and the distal end is located in the small intestine. The isolation element may have a proximal end and a distal end and wherein the isolation element is delivered such that the proximal end is located in the esophagus and the distal end is located in the pyloric canal. The isolation element of the method may have a proximal end and a distal end and wherein the isolation element is delivered such that both the proximal and distal ends are located in the small intestines. The isolation element may have a proximal end and a distal end and wherein the isolation element is delivered such that the proximal end is located distal of the pyloric valve and the distal end is located in the jejunum or ileum. The isolation element of the method may have a proximal end and a distal end and wherein the isolation element is delivered such that the proximal end is located distal of the orifice of the common bile duct. The wall of the isolation element of the method may have a wall thickness of between about 0.013 and 0.038 cm (0.0005 to 0.015 inches). The length of the isolation element may have a length in the range of about 60 to 600 cm.

The step of attaching the isolation element to tissue in the method of isolating tissue in the digestive tract may include expanding a balloon to place the isolation element into contact with the tissue.

In another aspect the present invention is a method of isolating tissue in the digestive tract. The method includes delivering a plurality of nanostructures to a desired location in the digestive system. The method also includes attaching the nanostructures to tissue at the desired location.

The nanostructures of the method of isolating tissue in the digestive tract may have nano-spheres. The nanostructures of the method may have a size in the range of about 5 to 750 nanometers and/or may have a density in the range of about 1 to 1000 nanostructures per square micrometer. The nanostructures may have a surface that is hydrophobic. The method of isolating tissue in the digestive tract may include incorporating the nanostructures into a dissolvable material and wherein the step of delivering a plurality of nanostructures to a desired location in the digestive system comprises placing the dissolvable material into contact with the tissue in the digestive system that is to be isolated and the dissolvable material may be sugar.

In another aspect this invention is a device for isolating tissue in the digestive system from food traveling through the digestive system. The device includes a biocompatible portion having a surface sized to cover the tissue to be isolated and also includes a plurality of micro-anchors attached to the biocompatible portion and extending from the surface, the micro-anchors sized to penetrate the mucosa of the tissue.

The device of isolating tissue in the digestive tract may include the biocompatible portion having a plurality of spaced apart cylindrical tubes. The plurality of cylindrical tubes may have a length in the range of about 2 to 8 cm and/or may be spaced apart by a distance in the range of about 1 to 4 cm. The plurality of cylindrical tubes may further include a proximal tube having proximal and distal ends and a distal tube having proximal and distal ends.

The biocompatible portion of the device of isolating tissue in the digestive tract may include at least one longitudinal strip of material or may include at least one patch of material. The at least one patch of material may have an irregular shape or may be sized to cover an area of tissue about 1 to 5 square centimeters.

The device of isolating tissue in the digestive tract may include that the biocompatible portion is a cylindrical tube that may further be provided with cutouts or open portions.

The device may include the micro-anchors being positioned about a proximal end of the biocompatible portion or may include the micro-anchors being positioned at discrete locations along the length of the biocompatible portion.

The device may include micro-anchors having a length in the range of about 0.013 to 0.254 cm (0.005 to 0.100 inches). The device may include that the micro-anchors have a transverse cross-sectional dimension in the range of about 0.003 to 0.038 cm (0.001 to 0.015 inches). The plurality of micro-anchors of the device may include about 500 to 3000 micro-anchors per square inch and/or the micro-anchors of the device may be made of stainless steel, Nitinol, or a polymer material. The micro-anchors may include protruding scales, the scales having tips that are oriented in a direction substantially opposite to the direction of tips of the micro-anchors. The micro-anchors may be U-shaped having first and second ends oriented in the same direction.

The biocompatible portion of the device of isolating tissue in the digestive tract may be made of silicone or polyurethane and/or may be bioabsorbable or biodegradable. The biocompatible portion of the method may include an internal surface and wherein the internal surface is lubricious. The wall of the biocompatible portion of the device may have a wall thickness of between about 0.013 and 0.038 cm (0.0005 to 0.015 inches). The length of the biocompatible portion may have a length in the range of about 60 to 600 cm.

DETAILED DESCRIPTION OF THE PREFERRED EMBODIMENTS

The present invention provides methods and devices for attaching an implant within the digestive tract. Although described primarily in the context of supporting an isolation element, the technology of the present invention can be utilized to support a variety of devices which may be positioned within the digestive tract or in any vessel, conduit or other location within a human body where it is desirable to attach a device or substance to tissue and where such attachment can not be feasibly accomplished using traditional techniques such as suturing, stapling or gluing. For example, this technology could be employed to support a variety of diagnostic devices, such as pH detectors or pressure sensors. It could be utilized to position valves or constricted openings designed to treat Gastroesophageal Reflux Disease (GERD). It could be employed to position leads of electrical stimulation and/or pacing devices. The device could be used in portions of the digestive tract to isolate a defect or disease condition, such as an ulceration, or other gastrointestinal anomaly.

Notwithstanding the foregoing, the present invention will be described primarily in the context of an isolation element for reducing nutrient absorption in the digestive tract and treating metabolic disorders, such as Type II diabetes. FIGS. 1 to 4 show various embodiments of isolation elements which can be used for the purpose of isolating tissue or selected portions of tissue in the digestive system from coming into contact with ingested food. FIGS. 5A to 5H show embodiments of attachment mechanisms which are used to attach the isolation elements to tissue in the digestive system. FIGS. 6A to 6D show an alternative means to isolate tissue in the digestive system comprising attaching to the tissue or targeted portions of the tissue a plurality of nanostructures such as nano-spheres which prevent the tissue from contacting ingested food. FIGS. 7A to 7E show a delivery system which can be used to deliver and deploy the various isolation elements disclosed herein within the digestive system.

Figure 1:
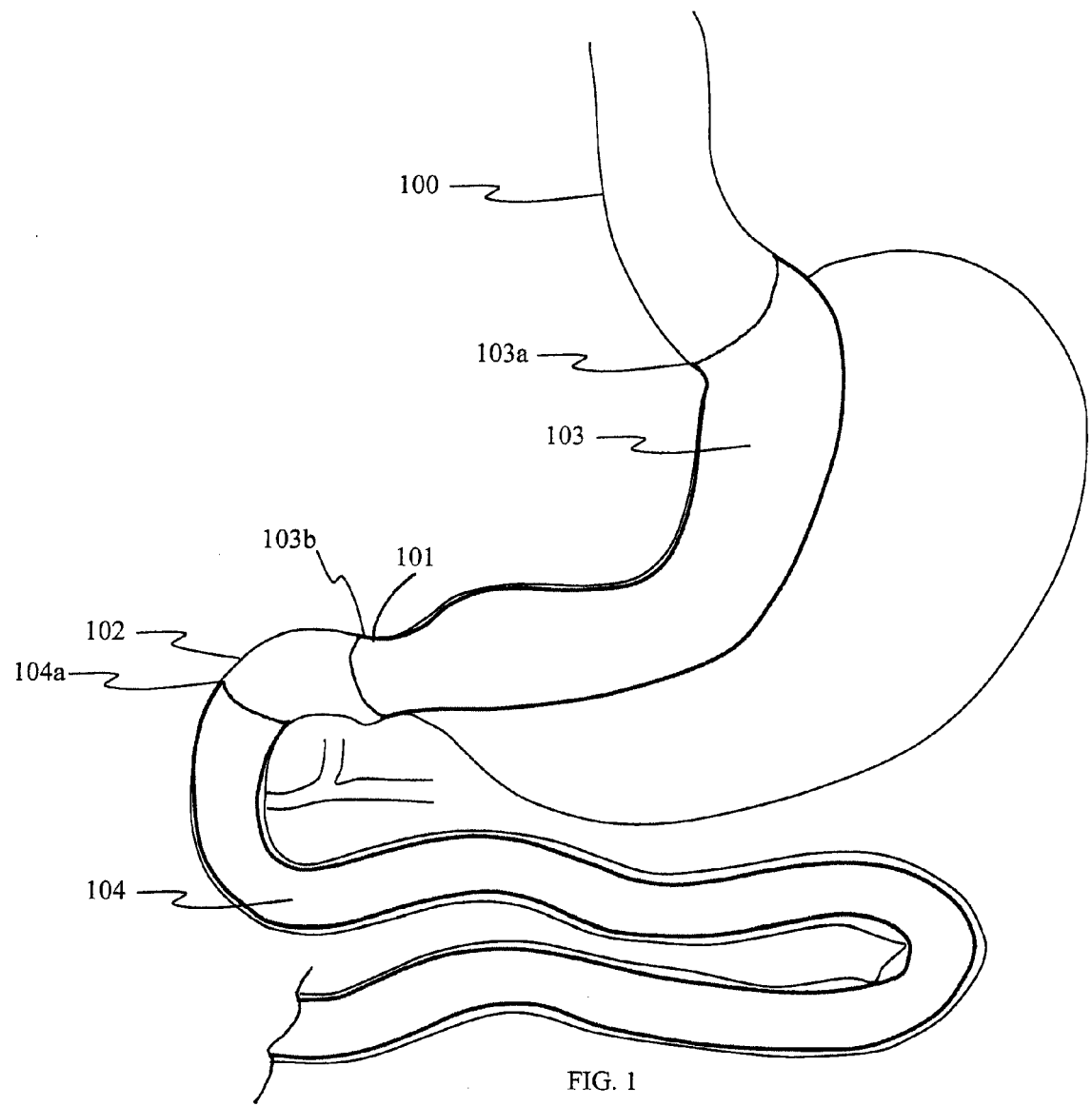
FIG. 1 shows an isolation element in two parts; one part with the proximal end in the esophagus and the other part with the proximal end distal of the pylorus.

FIG. 1 shows an isolation element 103 implanted within a patient. The proximal end 103a is shown in the esophagus 100 and the distal end 103b is shown in pyloric canal of the stomach 101. The isolation element 103 can have a fixed diameter opening equal to, larger or smaller than the fully open diameter at the native esophagus. It should be appreciated that the proximal end 103a could be located anywhere along the length of the esophagus and that the distal end 103b could be located in the stomach, near the pyloric valve, or through the pyloric valve and into the duodenum 102. Also shown is an isolation element 104 implanted in a patients small intestines. The proximal end 104a is shown in the duodenum 102 just distal of the pyloric valve. The distal end (not shown) extends down the small intestines and may end in the duodenum, jejunum or ileum. The isolation element 104 can have a fixed diameter opening equal to, larger or smaller than the fully open diameter at the native duodenum. Isolation elements 103 and 104 can be used individually, or together as a system depending on the needs of the patient.

The isolation element may be made from a suitable biocompatible material which is chemically resistant. Examples of suitable materials include polyurethane (Dow Pelathane) or silicone (Dow Silatstic). The wall thickness should be between 0.0005 and 0.015 inches (0.0013 to 0.038 cm). The diameter of the isolation element is selected to be compatible with the location of its use. For example, if the proximal portion of the isolation element is in the esophagus then the diameter may be between about 15-30 mm. If the proximal portion is in the duodenum the diameter may be between about 10-25 mm. The length of the isolation element is also selected to be appropriate for its intended application. For example, the length may be selected to be in the range from about 60 to 600 cm. The isolation element may be made from biocompatible material that is biodegradable. For example, polymers such as Polyester based on polylactide (PLA), polyglycolide (PGA), polycaprolactone (PCL), and their copolymers have been extensively employed as biomaterials which can biodegrade over time. Newer classes of biodegradable polymers such as tyrosine polyarylates could also be used.

Figure 2:
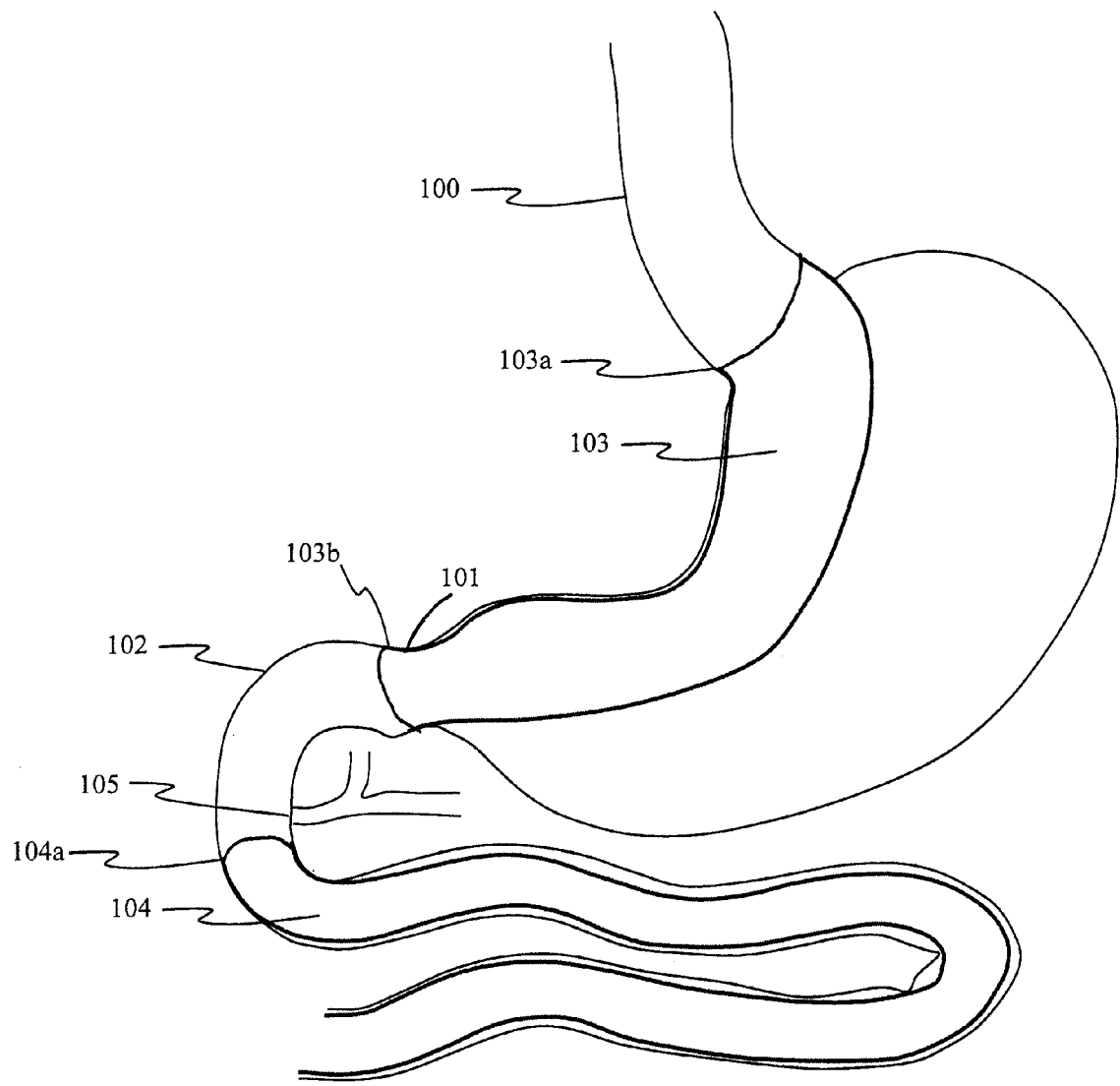
FIG. 2 shows an isolation element in two parts; one part with the proximal end in the esophagus and the other part with the proximal end distal of the orifice of the common bile duct and pancreatic duct.

FIG. 2 shows isolation elements 103 and 104 implanted within a patient in an alternative manner. In this embodiment isolation element 103 is implanted within the patient in a manner and location similar to that described in connection with FIG. 1. However, isolation element 104 is implanted in a more distal location in the patient's small intestines. In this embodiment the proximal end 104a is shown in the duodenum 102 just distal of the orifice of the common bile duct and pancreatic duct 105. The distal end (not shown) extends down the small intestines and may end in the duodenum, jejunum or ileum. The isolation element 104 can have a fixed diameter opening equal to, larger or smaller than the fully open diameter at the native duodenum.

Figure 3:
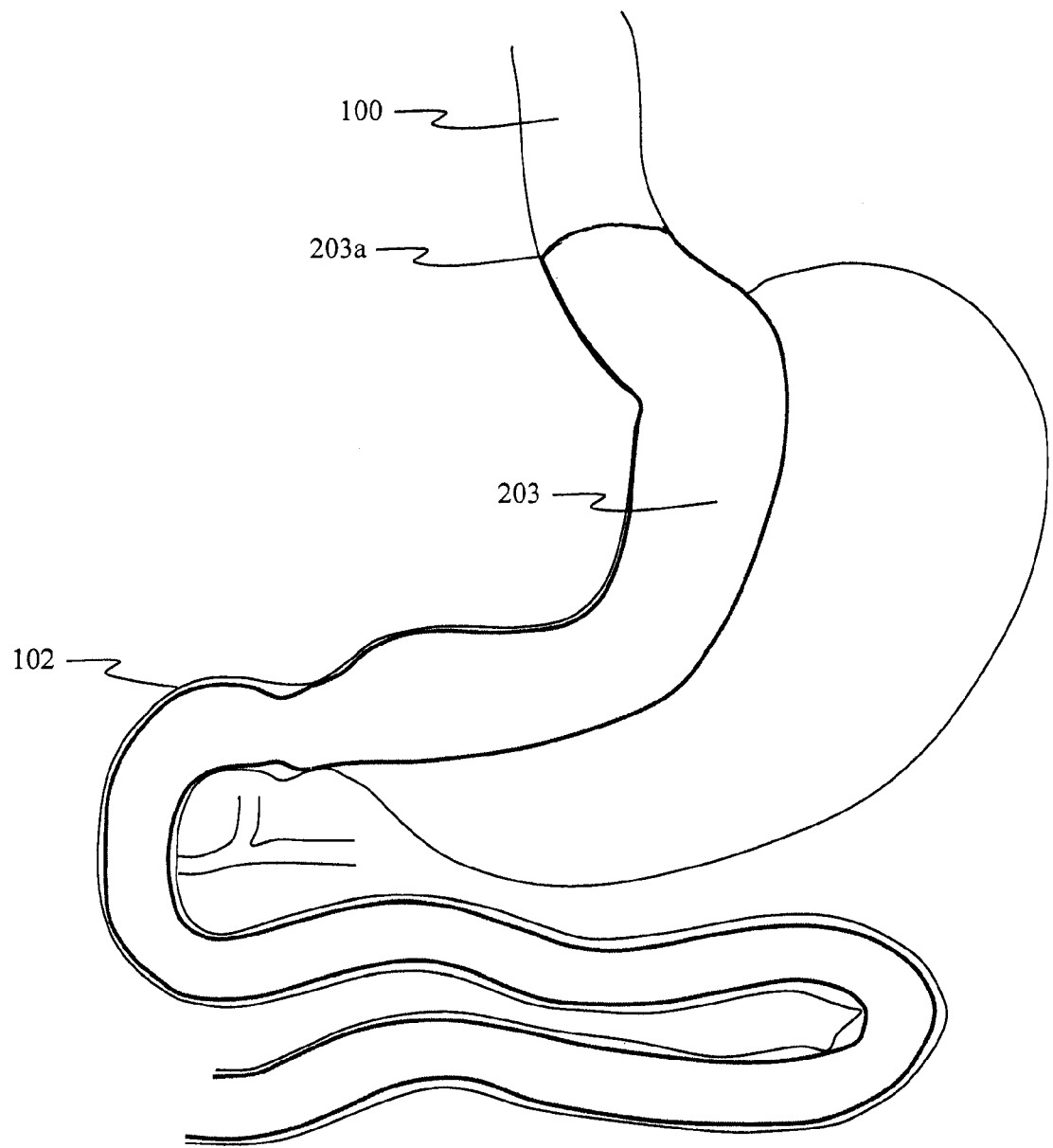
FIG. 3 shows another embodiment of an isolation element with the proximal end in the esophagus and the distal end in the small intestines.

FIG. 3 shows an embodiment which uses a single isolation element 203 as an alternative to the use of multiple isolation elements such as those shown in FIGS. 1 and 2. The proximal end 203a of the isolation element is shown implanted in the esophagus 100. The distal end (not shown) extends down the small intestines and may end in the duodenum, jejunum or ileum. The isolation element 203 can have a fixed diameter opening equal to, larger or smaller than the fully open diameter at the native esophagus. It should be appreciated that the proximal end 203a could be located anywhere along the length of the esophagus. The use of a single isolation element simplifies the delivery and deployment of the isolation element since the physician only has to deploy one device instead of two. Further, it is believed that the delivery and deployment of a single device in the esophagus will be less challenging than delivering and deploying multiple devices including at least one more distally into the duodenum. FIGS. 4A, 4B, 4C and 4D show alternative embodiments of the invention which may be used to selectively isolate portions of the digestive system. The portions of the digestive system that are not isolated continue to function in a normal manner.

Figure 4A:
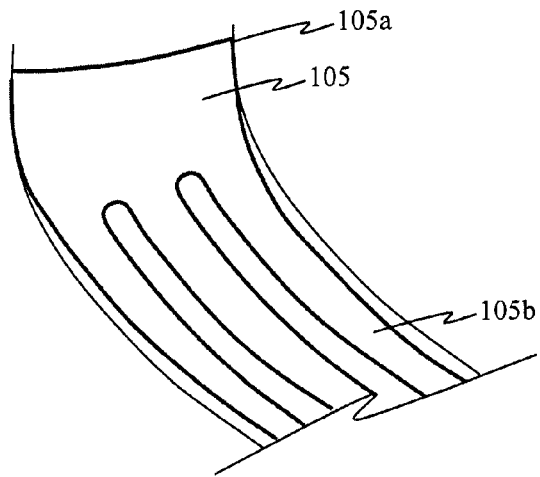
FIG. 4A shows a portion of a further embodiment of an isolation element with longitudinal strips

FIG. 4A shows a segment of an isolation element 105. The proximal portion 105a is shown as a continuous, relatively cylindrical element. Strips of material 105b extend distally. These strips are secured to the mucosal side of the wall of the digestive system using the attachment mechanism described hereafter in connection with FIGS. 5A to 5H. They provide a barrier to effectively isolate the tissue, in the region that they are secured, from anything traveling through digestive system. The strips may be secured to the tissue over the entire surface of the strip or on the edges of the strips.

Figure 4B:
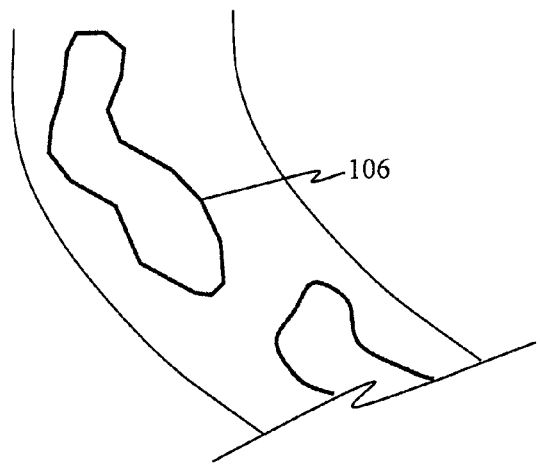
FIG. 4B shows a portion of another embodiment of isolation elements configured as irregularly shaped patches.

FIG. 4B shows isolation elements 106 attached at selected locations within the digestive system. One or more such isolation elements may be employed to selectively isolate portions of the digestive system. Isolation elements 106 may be secured to the tissue over the entire surface of the element or at the edges of the element. The isolation elements 106 may be irregularly shaped patches. Each may have the same shape or they may be of different shape. The number and size of the isolation elements used in a particular procedure are varied depending on the needs of the patient. If it is desired to isolate a significant amount of tissue more and/or larger isolation elements are used as compared to a situation where less of the digestive system tissue must be isolated. For example, an isolation element 106 may be sized to cover and isolate an area from about 1 to 5 square cm. However, the size could be greater or less depending on the circumstances.

Figure 4C:
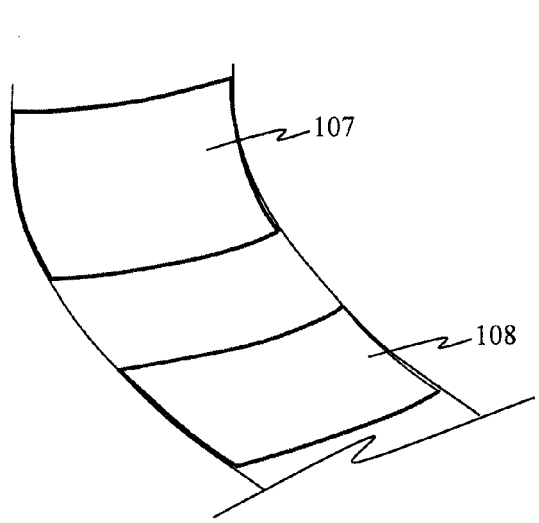
FIG. 4C shows a portion of a further embodiment of an isolation element configured in a series of finitely spaced segments.

FIG. 4C shows isolation elements 107 and 108 attached at selected locations within a digestive system. Although the entire surface of the isolation elements is shown as a continuous, relatively cylindrical element, windows or cutouts as described in connection with FIG. 4D could be provided if desired. Isolation elements 107 and 108 may be secured to the tissue over the entire surface of the element or at the edges of the element. Isolation element 108 is shown a discrete distance away from element 107. This has the effect of isolating portions of the tissue of the digestive system while leaving other portions exposed. It should be appreciated that this pattern could be repeated by using two or more isolation elements to isolate as much digestive system tissue as desired. The diameter of the isolation elements is selected to be compatible with the location within the digestive system where they are to be deployed. The length of the isolation elements may be in the range of about 2 to 8 cm. The spacing between isolation elements may be in the range of about 1 to 4 cm depending on how much tissue is desired to be isolated.

Figure 4D:
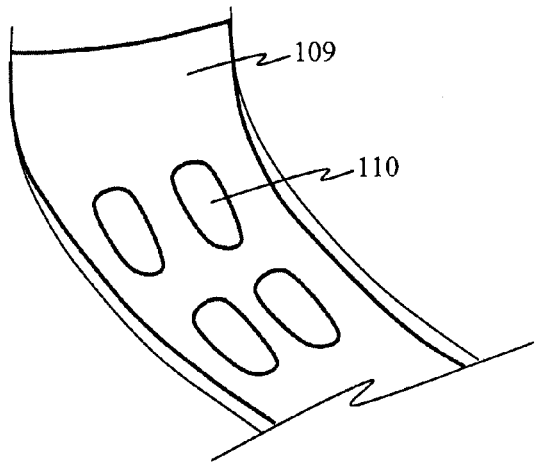
FIG. 4D shows a portion of another embodiment of an isolation element configured with cutouts.

FIG. 4D shows an isolation element 109. Windows or cutouts 110 are shown. These windows have the effect of exposing discrete areas of the digestive system wall tissues. The areas along the length of the isolation element that are not in the vicinity of a window 110 will be isolated from anything passing through the digestive system. This can be achieved by securing the isolation element to the tissue around the edges of the windows 110. It should be appreciated that the pattern of windows, the size of the windows, and the number of windows can be varied to create the desired effect.

Figure 5A:
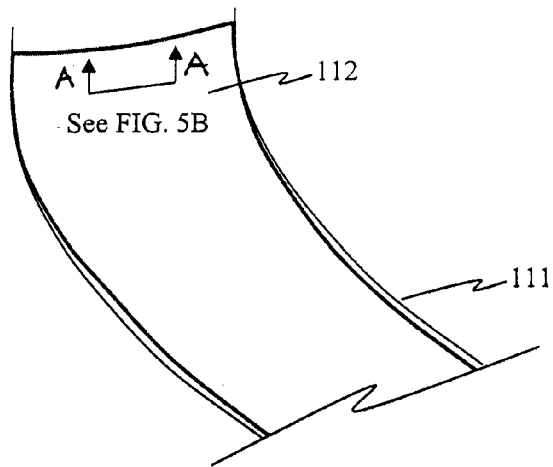
FIG. 5A shows a portion of an isolation element attached to tissue in the digestive system.

FIG. 5A shows a portion of an isolation element 112 and a portion of the digestive system 111. Isolation element 112 is meant to represent any of the various embodiments of isolation elements previously described for the purpose of showing how these isolation elements may be attached to the interior wall of the digestive system 111.

Figure 5B:
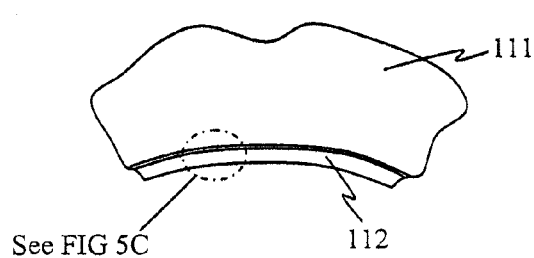
FIG. 5B shows a cross section of a portion of the isolation element of FIG. 5A.

FIG. 5B shows a cross-sectional portion along line A-A of FIG. 5A. The isolation element 112 is shown adjacent to the mucosal side of the wall 111 of the digestive system.

Figure 5C:
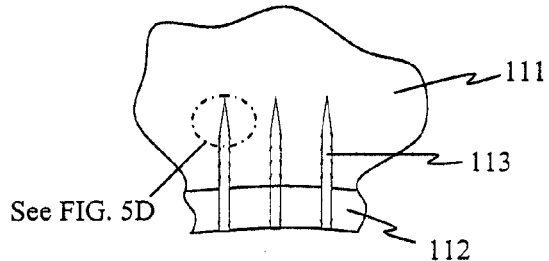
FIG. 5C shows an enlarged portion of the cross section of FIG. 5B

FIG. 5C shows an enlarged portion of the cross section of FIG. 5B. The isolation element 112 is shown adjacent to the mucosal side of the wall 111 of the digestive system. Miniature elements or micro-anchors 113 are shown attached to isolation element 112. These micro-anchors fix the isolation element to the tissue. The micro-anchors are about 0.005 to 0.100 inches (0.013 to 0.254 cm) in length and have a transverse cross-sectional dimension no greater than about 0.001 to 0.015 inches (0.006 to 0.038 cm). A plurality of micro-anchors are distributed over a relatively large area of the isolation element. This has the effect of distributing the holding force of the isolation element to the tissue, while maintaining a flexible compliant system. For example, the isolation elements may include between about 500 and 3000 micro-anchors per square inch if the entire surface of the isolation element is to be attached to the tissue. The micro-anchors may be made from suitable biocompatible materials including, for example, stainless steel, Nitinol, or a suitable polymer such as Polyester.

Figure 5D:
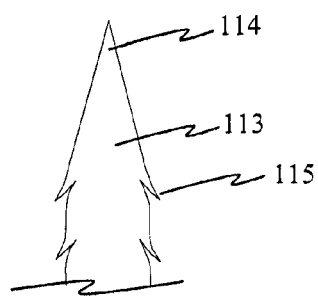
FIG. 5D shows an enlarged portion of the micro-anchors of FIG. 5C.
Figure 5E:
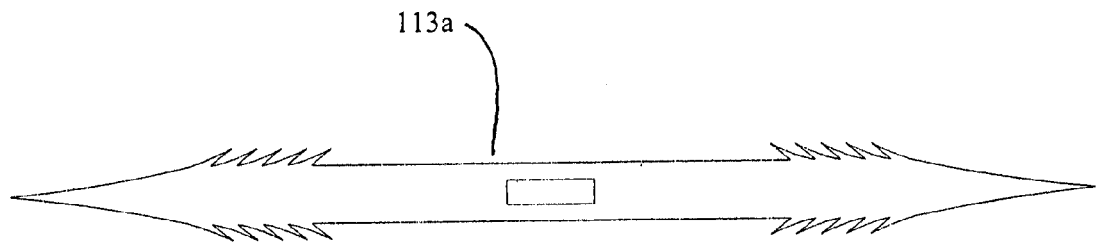
FIG. 5E shows an alternative embodiment of the micro-anchors.
Figure 5F:
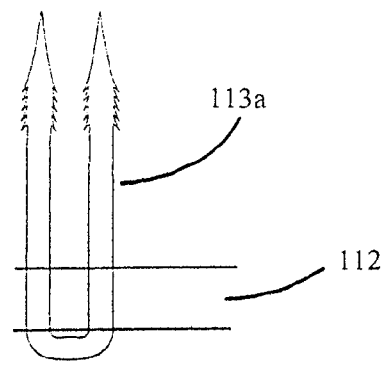
FIG. 5F shows the micro-anchor of FIG. 5E connected to the isolation element.

FIG. 5D shows a portion of the micro-anchors 113. Optimally the leading edge 114, that first penetrates the tissue, has a relatively sharp tip. Protruding scale like features 115 are positioned along the sides or circumference of the micro-anchors and have tips that are oriented in a direction substantially opposite to that of the tip of the micro-anchor. These features engage the tissue and resist movement of the micro-anchor out of the tissue. There is a plurality of these features on each micro-anchor. For example there may be about 3 to 20 of the features per micro-anchor or 3 to 60 of the features in the case of an embodiment with multiple overlapping features such as shown in FIG. 5H. These features protrude from the surface of the anchor from 0.0005 to 0.005 inches (0.0013 to 0.013 cm). This has the effect of distributing and increasing the holding force along and around the micro-anchor by engaging the tissue in many locations.

Figure 5G:
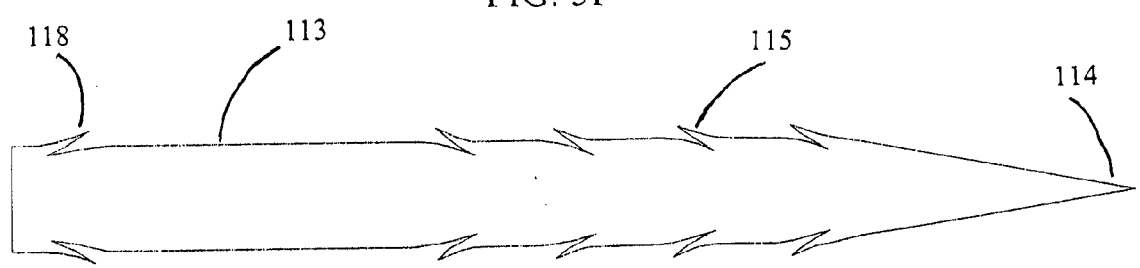
FIG. 5G is an enlarged view of a micro-anchor of FIG. 5C.
Figure 5H:
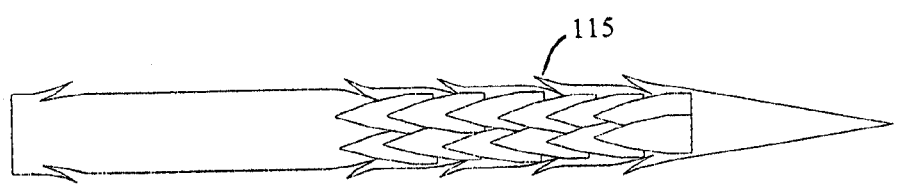
FIG. 5H shows another embodiment of the micro-anchors.

FIG. 5G is an enlarged view of micro-anchor 113 and shows the manner in which micro-anchor 113 is attached to the isolation element. Specifically, scale like features 118 are positioned adjacent the end of the micro-anchor opposite tip 114. Features 118 have tips which are oriented in the same direction as tip 114 and opposite the direction of the tips of features 115. This configuration allows the tip 114 of the micro-anchors to be driven through the wall of the isolation element. Tips 118 prevent the micro-anchors from being drawn all the way through the isolation element and effectively fix the micro-anchors to the isolation element. When attached the micro-anchors 113 may be substantially perpendicular to the isolation element and parallel to each other or they may be attached at an angle. As shown in FIG. 5H scale like features 115 may optionally be positioned in an overlapping configuration.

Another manner of attaching the micro-anchors to the isolation element is shown in FIGS. 5E and 5F. FIG. 5E shows a double ended micro-anchor 113a having a sharp tip at both ends. The double ended micro-anchor is bent or folded in half to form a U shape. The tips of the folded anchor are driven through the wall of the isolation element until the bottom of the U shaped portion engages the wall of the isolation element as shown in FIG. 5F. Thus, both ends of the double ended micro-anchor comprising proximal and distal portions extend from the isolation element and are locked in place by the engagement of the intermediate U shaped portion with the wall of the isolation element. The proximal and distal portions may be parallel to each other in this configuration or angled.

The various embodiments of the micro-anchors have a length which allows them to penetrate and be embedded in the mucosa in order to securely attach the isolation elements. Alternatively, they may have a length which allows them to penetrate into the submucosa or muscular layers.

Figure 6A:
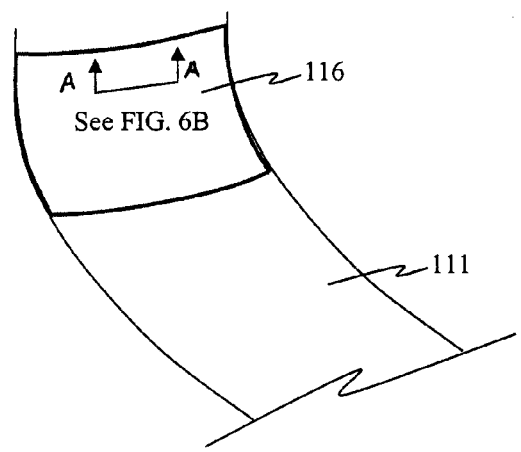
FIG. 6A shows a portion of an isolation element carrier deployed in the digestive system.
Figure 6B:
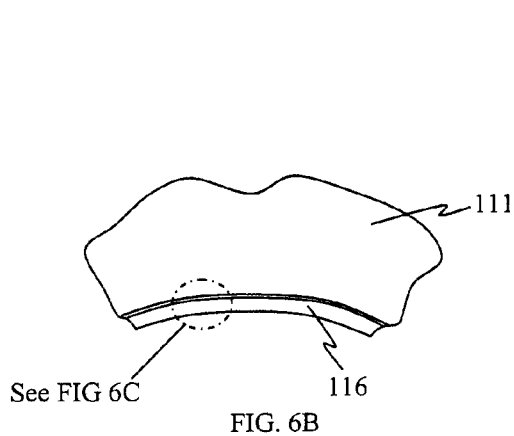
FIG. 6B is a partial cross section of FIG. 6A.

FIG. 6A shows a portion of an isolation element carrier 116 and a portion of the digestive system 111. Isolation carrier element 116 is used to assist in the delivery of an alternative embodiment of an isolation element within the digestive system. FIG. 6B shows a cross-sectional portion of FIG. 6A along line A-A which illustrates the isolation element carrier 116 positioned against the tissue of digestive tract 111.

Figure 6C:
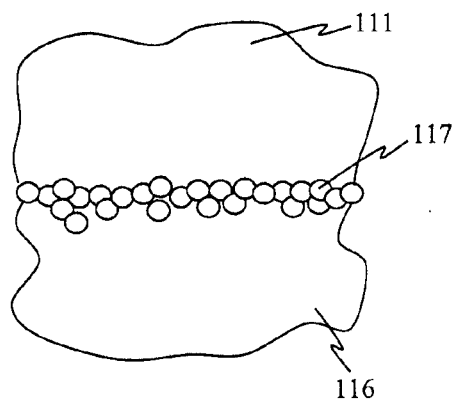
FIG. 6C is an enlarged view of a portion of the cross section of FIG. 6B.

FIG. 6C shows an enlarged portion of the cross section of FIG. 6B. The carrier element 116 is a readily dissolvable material, such as sugar, which has in it or on the surface of it the isolation element 117. The isolation element 117 is a nano-technology comprising nanostructures such as nanospheres, which will adhere to the tissue of the digestive tract in gecko like fashion due to Vanderwalls forces. There is provided in accordance with one aspect of the present invention, an isolation element which is made up entirely of a nanostructure. Nanostructures may have a variety of shapes and may comprise nanoparticles, nanotubes, nanofibers, nanodots, nanotetarapods, nanospheres, etc. The size of the nanostructures may be in the range of about 5 nanometers to 750 nanometers. The density of the nanostructures typically ranges from between about 1 to 1000 nanostructures per square micrometer. It is well understood to those familiar to this field that nanostructure surfaces can be engineered to produce a variety of characteristics. A nanostructure surface can be engineered to be hydrophobic or treated to be superhydrophobic, excluding water completely. In this embodiment the surface of the nanostructure that is in contact with the wall of the digestive tract is engineered to have the characteristics of a dry adhesive i.e. the so called "gecko effect". This would have the effect of adhering the nanostructure to the wall of the digestive tract. The surface of the nanostructure facing away from the wall of the digestive tract i.e. the surface exposed to fluids and ingested materials would be engineered to be hydrophobic. This would have the effect of restricting solutions/ingested materials from contacting the underlying tissue, in effect creating a barrier.

Figure 6D:
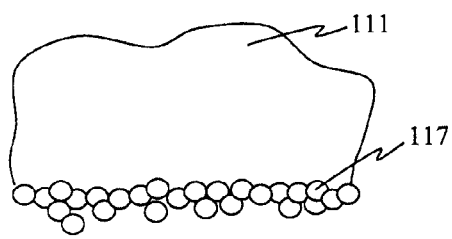
FIG. 6D shows the cross section of FIG. 6C after the carrier element has dissolved.

The nanostructure is incorporated into a dissolvable material and is delivered by placing the material in contact with the tissue in the digestive system that is to be isolated from food contact. The dissolvable material dissolves leaving behind the nanostructure which remains attached to the tissue. The carrier element 116 delivers the isolation elements to the desired location in the digestive tract and then optimally dissolves with in seconds to minutes of exposure to the digestive system environment. The areas of the digestive tract that have the isolation elements adhered to them will be isolated from anything traveling through the digestive tract. FIG. 6D shows the section of FIG. 6C after the carrier element 116 has dissolved.

The various embodiments of the isolation elements disclosed herein may be delivered and deployed within the digestive system in any conventional manner. For example, the isolation elements can be delivered using a delivery system as shown in FIGS. 7A to 7E. The delivery system includes a catheter 200 which has a distal balloon expandable portion 202. The catheter 200 includes a central lumen 204 and an inflation lumen 206. The balloon expandable portion is shown in a deflated configuration in FIG. 7A and in an inflated configuration in FIG. 7B. The balloon expandable portion is sized to have an inflated diameter which is sufficient to enable it to be used to deliver and deploy the isolation elements disclosed herein within the digestive system. For example, the inflated diameter of the balloon expandable portion may be in the range of about 10 to 30 mm. The longitudinal length of the balloon expandable portion is selected to be appropriate for the isolation element which is to be deployed. Since the isolation elements disclosed herein have a wide range of sizes the length of the balloon expandable portion will be in the range of about 10 mm to 30 cm. The isolation elements are mounted for delivery over the balloon expandable portion of the catheter while the balloon is deflated. The catheter is introduced into the digestive system through the esophagus and positioned at a desired location. The balloon expandable portion is then inflated to cause the isolation element or elements to contact the tissue of the digestive system at the desired location. Once the isolation element or elements are properly attached to the tissue the balloon expandable portion is deflated and the catheter is withdrawn from the patient.

Figure 7A:
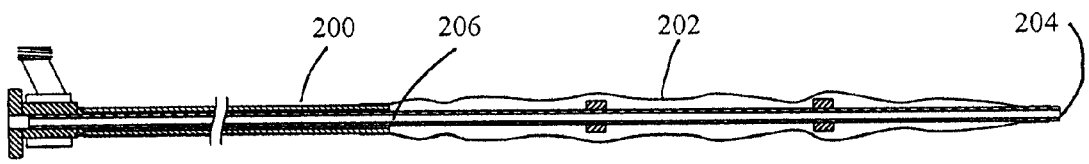
FIG. 7A is a cross sectional view of a delivery catheter having a balloon expandable distal portion.
Figure 7B:
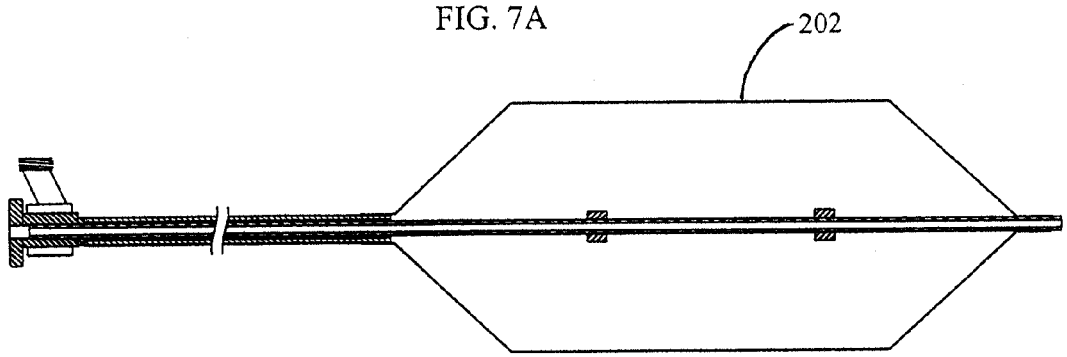
FIG. 7B shows the delivery catheter of FIG. 7A with the balloon expandable distal portion expanded.
Figure 7C:
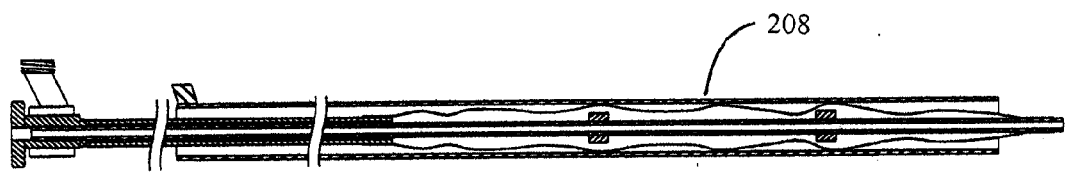
FIG. 7C shows a delivery system which includes the catheter of FIG. 7A within an outer sheath.
Figure 7D:
FIG. 7D shows the delivery system of FIG. 7C with the balloon expandable portion extending from the distal end of the sheath.
Figure 7E:
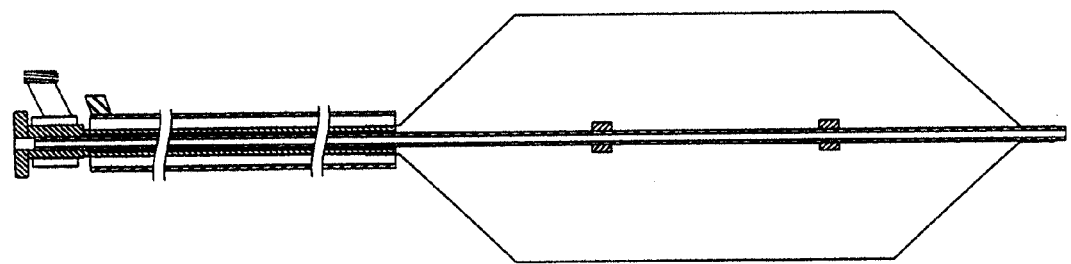
FIG. 7E is a view similar to FIG. 7D with the balloon expandable portion expanded.

As shown in FIG. 7C the delivery system may optionally include a sheath 208 to further ensure that the balloon expandable portion remains contracted and to protect the isolation elements from being dislodged during delivery. The sheath is pulled back to expose the isolation element when in the correct location in the anatomy as shown in FIG. 7D. Once the sheath is pulled back the balloon expandable portion is expanded as shown in FIG. 7E to deploy and fix the isolation element or elements to the tissue of the digestive system.

To fix smaller pieces in place during deployment such as the isolation elements 106 of FIG. 4B a wax or temporary glue may be employed to hold them to the balloon expandable portion until the balloon expandable portion is expanded and they are attached to the tissue. Alternatively, the plurality of isolation elements may be held together and mounted on the balloon expandable portion by a cylindrical mesh or weblike structure made of threads which may be biodegradable.

In one embodiment for delivering an isolation element the isolation element might be rolled up, length wise from the distal end to the proximal end. During the deployment process the isolation element is exposed by pulling back on the sheath. The balloon is then expanded to press a proximal portion of the isolation element against the tissue to anchor it. A fluid is then injected into the central lumen of the catheter. The fluid flows through the isolation element. The fluid pressure has the affect of unrolling the remaining distal portion of the isolation element. As the isolation element unrolls the unattached portion travels distally down the digestive tract. Once unrolled the isolation element remains unrolled and generally in a configuration that conforms to the anatomy. As an alternative to using fluid to unroll the isolation element a blunt ended flexible rod may be used. The rod is inserted and advanced through the central lumen past the distal end of the catheter to unroll the isolation element. It should be understood that in these embodiments for delivery of the isolation element, it is not necessary to use the central lumen of the delivery catheter to deliver or direct fluid or the blunt ended flexible rod through the isolation element in order to unroll it. Specifically, after the proximal portion has been anchored the balloon may be deflated and the catheter withdrawn. After the balloon is deflated and/or after the catheter is withdrawn either fluid or a blunt ended flexible rod may be introduced through the isolation element to unroll the unattached portion of the isolation element.

The isolation elements comprising nanostructures such as nano-spheres or nano-particles are delivered and deployed in a similar manner. A readily dissolvable material, such as sugar, can be configured to form a tube. This tube can be coated with nano-particles. The coated tube, as described above, can be implanted with a balloon delivery system. Specifically, the tube is mounted on the balloon expandable portion and delivered to a desired location in the digestive system. The sheath is then withdrawn and the balloon expandable portion is expanded to cause the nano-spheres to contact the tissue. Once in place the digestible material dissolves and the nano-particles are left behind forming a barrier between ingested materials and the wall of the digestive tract.

What is claimed is:

1. A method of isolating tissue in the digestive tract comprising: delivering an isolation element to a desired location in the digestive system, the isolation element having fixed thereto a plurality of micro-anchors; and attaching the isolation element to tissue at the desired location by causing pointed tips of the micro-anchors to penetrate the mucosa of the tissue, wherein each of the plurality of micro-anchors comprises protruding scales, each scale having a single tip that is oriented in a direction substantially opposite to the direction of the pointed tip of the micro-anchor, and the scales overlap, these scales engage the tissue and resist movement of the micro-anchor out of the tissue, and the micro-anchors being fixed attached to the isolation element, the isolation element includes 500-3000 micro-anchors per square inch of the area of the isolation element comprising micro-anchors.

2. The method of claim 1 wherein the isolation element comprises a cylindrical tube.

3. The method of claim 1 wherein the isolation element comprises a plurality of spaced apart cylindrical tubes.

4. The method of claim 3 wherein the isolation element comprises a proximal tube having proximal and distal ends and a distal tube having proximal and distal ends.

5. The method of claim 4 wherein the isolation element is delivered such that the distal end of the proximal tube is located in the pyloric canal.

6. The method of claim 4 wherein the isolation element is delivered such that the proximal end of the distal tube is located distal to the pyloric valve.

7. The method of claim 4 wherein the isolation element is delivered such that the proximal end of the distal tube is located distal of the orifice of the common bile duct.

8. The method of claim 1 wherein the isolation element comprises at least one longitudinal strip of material.

9. The method of claim 1 wherein the isolation element comprises at least one patch of material.

10. The method of claim 9 wherein the at least one patch is sized to cover an area of tissue about 1 to 5 square centimeters.

11. The method of claim 2 wherein the cylindrical tube is provided with cutouts or open portions.

12. The method of claim 1 wherein the micro-anchors are positioned about a proximal end of the isolation element.

13. The method of claim 1 wherein the micro-anchors are positioned at discrete locations along the length of the isolation element.

14. The method of claim 1 wherein the isolation element comprises silicone or polyurethane.

15. The method of claim 1 wherein the isolation element is bioabsorbable or biodegradable.

16. The method of claim 1 wherein the isolation element includes an internal surface and wherein the internal surface is lubricious.

17. The method of claim 1 wherein the isolation element has a proximal end and a distal end and wherein the isolation element is delivered such that the proximal end is located in the esophagus and the distal end is located in the small intestine.

18. The method of claim 1 wherein the isolation element has a proximal end and a distal end and wherein the isolation element is delivered such that the proximal end is located in the esophagus and the distal end is located in the pyloric canal.

19. The method of claim 1 wherein the isolation element has a proximal end and a distal end and wherein the isolation element is delivered such that both the proximal and distal ends are located in the small intestines.

20. The method of claim 1 wherein the isolation element has a proximal end and a distal end and wherein the isolation element is delivered such that the proximal end is located distal of the pyloric valve and the distal end is located in the jejunum or ileum.

21. The method of claim 1 wherein the isolation element has a proximal end and a distal end and wherein the isolation element is delivered such that the proximal end is located distal of the orifice of the common bile duct.

22. The method of claim 1 wherein the isolation element comprises a wall having a wall thickness of between about 0.0005 and 0.015 inches.

23. The method of claim 1 wherein the isolation element has a length in the range of about 60 to 600 cm.

24. The method of claim 3 wherein the plurality of cylindrical tubes have a length in the range of about 2 to 8 cm.

25. The method of claim 3 wherein the plurality of cylindrical tubes are spaced apart by a distance in the range of about 1 to 4 cm.

26. The method of claim 1 wherein the micro-anchors have a length in the range of about 0.005 to 0.100 inches.

27. The method of claim 1 wherein the micro-anchors have a transverse cross-sectional dimension in the range of about 0.001 to 0.015 inches.

28. The method of claim 1 wherein the micro-anchors comprise stainless steel, Nitinol, or a polymer material.

29. The method of claim 1 wherein the micro-anchors are U-shaped having first and second ends oriented in the same direction.

30. The method of claim 1 wherein the step of attaching the isolation element to tissue comprises expanding a balloon to place the isolation element into contact with the tissue.

31. A device for isolating tissue in the digestive system from food traveling through the digestive system comprising: a biocompatible portion having a surface sized to cover the tissue to be isolated; and a plurality of micro-anchors attached to the biocompatible portion and extending from the surface, the micro-anchors having pointed tips sized to penetrate the mucosa of the tissue, wherein each of the plurality of micro-anchors comprises protruding scales, each scale having a single tip that is oriented in a direction substantially opposite to the direction of the pointed tip of the microanchor, and the scales overlap, these scales engage the tissue and resist movement of the micro-anchor out of the tissue, and the micro-anchors being fixedly attached to the biocompatible portion, the biocompatible portion includes 500-3000 micro-anchors per square inch of the area of the isolation element comprising microanchors.

32. The device of claim 31 wherein the biocompatible portion comprises a cylindrical tube.

33. The device of claim 31 wherein the biocompatible portion comprises a plurality of spaced apart cylindrical tubes.

34. The device of claim 33 wherein the biocompatible portion comprises a proximal tube having proximal and distal ends and a distal tube having proximal and distal ends.

35. The device of claim 31 wherein the biocompatible portion comprises at least one longitudinal strip of material.

36. The device of claim 31 wherein the biocompatible portion comprises at least one patch of material.

37. The device of claim 36 wherein the at least one patch is sized to cover an area of tissue about 1 to 5 square centimeters.

38. The device of claim 32 wherein the cylindrical tube is provided with cutouts or open portions.

39. The device of claim 31 wherein the micro-anchors are positioned about a proximal end of the biocompatible portion.

40. The device of claim 31 wherein the micro-anchors are positioned at discrete locations along the length of the biocompatible portion.

41. The device of claim 31 wherein the biocompatible portion comprises silicone or polyurethane.

42. The device of claim 31 wherein the biocompatible portion is bioabsorbable or biodegradable.

43. The device of claim 31 wherein the biocompatible portion includes an internal surface and wherein the internal surface is lubricious.

44. The device of claim 31 wherein the biocompatible portion comprises a wall having a wall thickness of between about 0.0005 and 0.015 inches.

45. The device of claim 31 wherein the biocompatible portion has a length in the range of about 60 to 600 cm.

46. The device of claim 33 wherein the plurality of cylindrical tubes have a length in the range of about 2 to 8 cm.

47. The device of claim 33 wherein the plurality of cylindrical tubes are spaced apart by a distance in the range of about 1 to 4 cm.

48. The device of claim 31 wherein the micro-anchors have a length in the range of about 0.005 to 0.100 inches.

49. The device of claim 31 wherein the micro-anchors have a transverse cross-sectional dimension in the range of about 0.001 to 0.015 inches.

50. The device of claim 31 wherein the micro-anchors comprise stainless steel, Nitinol, or a polymer material.

51. The device of claim 31 wherein the micro-anchors are U-shaped having first and second ends oriented in the same direction.

* * * * *